US009089255B2

(12) United States Patent
Kato (10) Patent No.: US 9,089,255 B2
(45) Date of Patent: Jul. 28, 2015

(54) ENDOSCOPE SYSTEM (75) Inventor: Shuichi Kato, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 132 days.

(21) Appl. No.: 13/452,336

(22) Filed: Apr. 20, 2012

(65) Prior Publication Data
US 2012/0209061 A1 Aug. 16, 2012

Related U.S. Application Data (63) Continuation of application No. PCT/JP2010/066954, filed on Sep. 29, 2010.

(30) Foreign Application Priority Data

Oct. 23, 2009 (JP) .................................. 2009-244377

(51) Int. Cl.
*A61B 1/00* (2006.01)
*A61B 1/04* (2006.01)
(Continued)

(52) U.S. Cl.
CPC ......... *A61B 1/00124* (2013.01); *A61B 1/00114* (2013.01); *A61B 1/05* (2013.01)

(58) Field of Classification Search
CPC ........... A61B 1/00112; A61B 1/00114; A61B 1/00121; A61B 1/00124; A61B 1/00011; A61B 1/00016; A61B 1/0684; A61B 2017/0221
USPC .................. 600/109, 132, 133, 146, 160, 182
See application file for complete search history.

(56) References Cited

U.S. PATENT DOCUMENTS 4,325,606 A 4/1982 Ikuno et al.
4,868,647 A 9/1989 Uehara et al.
(Continued)

FOREIGN PATENT DOCUMENTS

CN 101282679 A 10/2008
CN 100446712 C 12/2008
(Continued)

OTHER PUBLICATIONS

International Search Report of PCT/JP2010/066954, mailing date of Nov. 2, 2010.
(Continued)

*Primary Examiner* — Anhtuan T Nguyen
*Assistant Examiner* — William Chou
(74) *Attorney, Agent, or Firm* — Westerman, Hattori, Daniels & Adrian, LLP (57) ABSTRACT

An endoscope system includes an endoscope having an insertion part capable of being be inserted into the interior of a living body; an extracorporeal device configured to be installed outside the living body, a first extracorporeal signal connection part having a second electrode electrically connected to the extracorporeal device, and a first scope-side signal connection part that has a first electrode electrically connected to the endoscope, is engaged with the first extracorporeal signal connection part, and has a tubular shape. The insertion part includes an observation part capable of observing a distal end side thereof. When engaged with the first scope-side signal connection part, the first extracorporeal signal connection part is at least partially disposed in an inner cylindrical space of the first scope-side signal connection part, and the second electrode and the first electrode are subjected to capacitive coupling.

10 Claims, 7 Drawing Sheets (51) Int. Cl.
*A61B 1/06* (2006.01)
*A61B 1/05* (2006.01)

(56) References Cited

U.S. PATENT DOCUMENTS

| | | | |
|---|---|---|---|
| 6,099,465 | A | 8/2000 | Inoue |
| 2002/0135361 | A1* | 9/2002 | Jagiella et al. ............ 324/207.26 |
| 2005/0148819 | A1* | 7/2005 | Noguchi et al. ............... 600/133 |
| 2005/0228268 | A1* | 10/2005 | Cole ............................. 600/420 |
| 2006/0116550 | A1 | 6/2006 | Noguchi et al. |
| 2006/0116552 | A1 | 6/2006 | Noguchi et al. |
| 2007/0078304 | A1* | 4/2007 | Shimizu et al. ................ 600/132 |
| 2007/0185385 | A1* | 8/2007 | Noguchi et al. ............... 600/132 |
| 2009/0110111 | A1 | 4/2009 | Kato et al. |
| 2010/0200636 | A1* | 8/2010 | Zemlok et al. .............. 227/175.1 |
| 2011/0306836 | A1* | 12/2011 | Ohline et al. ................. 600/146 |

FOREIGN PATENT DOCUMENTS

| | | |
|---|---|---|
| CN | 102395309 A | 3/2012 |
| JP | 55-078932 A | 6/1980 |
| JP | 64-072724 A | 3/1989 |
| JP | 07-191268 A | 7/1995 |
| JP | 10-155740 A | 6/1998 |
| JP | 2000340290 A | 12/2000 |
| JP | 2006-14127 A | 1/2006 |
| JP | 2006320381 A | 11/2006 |
| JP | 2007097767 A | 4/2007 |
| JP | 2009111497 A | 5/2009 |
| JP | 2010-252848 A | 11/2010 |
| WO | 2005/077249 A1 | 8/2005 |
| WO | 2005/077250 A1 | 8/2005 |

OTHER PUBLICATIONS

Japanese Office Action dated Dec. 17, 2013, issued in corresponding Japanese Patent Application No. 2009-244377 with English translation (6 pages).

Chinese Office Action dated Dec. 30, 2013, issued in Chinese Patent Application No. 201080046363.9 with English translation (19 pages).

* cited by examiner

ENDOSCOPE SYSTEM

This application is a continuous application based on a PCT Patent Application No. PCT/JP2010/066954 filed on Sep. 29, 2010, whose priority is claimed on Japanese Patent Application No. 2009-244377 filed on Oct. 23, 2009. The contents of both the PCT Application and the Japanese Patent Application are incorporated herein by reference.

BACKGROUND OF THE INVENTION

1. Field of the Invention

The present invention relates to an endoscope system that transmits a signal by means of a capacitive coupling.

2. Description of Related Art

Conventionally, endoscope systems generally include an endoscope having an insertion part inserted into the interior of a living body, and an extracorporeal device such as a monitor installed outside the living body. To transfer a signal between the endoscope and the extracorporeal device, electrodes installed on both the endoscope and the extracorporeal device are brought into direct contact with each other. Thus, a control signal or an image signal is transferred.

When the insertion part is inserted into the living body, a fluid from the living body is attached to the insertion part. As such, after the endoscope is used, the whole endoscope including a scope-side connector (first scope-side signal connection part) connected to the extracorporeal device needs to be sterilized, for instance, by cleaning equipment. Further, although the extracorporeal device has a low possibility of the fluid from the living body being attached thereto, the extracorporeal device is required to be kept clean in order to prevent infection. Particularly, since an extracorporeal connector (first extracorporeal signal connection part) of the extracorporeal device which is connected to the scope-side connector has a high chance of coming in contact with a person, it is necessary to keep the extracorporeal connector clean at all times by wiping it with an antiseptic solution.

For this reason, as disclosed, for example, in Japanese Unexamined Patent Application, First Publication No. 2007-097767, an electronic endoscope system (endoscope system) that transfers a signal by means of capacitive coupling without bringing electrodes into direct contact with each other has been proposed.

In the electronic endoscope system, a universal cord provided to an intracorporeal device (endoscope) is connected to an extracorporeal device. A pair of mutually detachable connectors (signal connection parts) is installed on connection parts of the universal cord and the extracorporeal device. The connector of the intracorporeal device includes a first circular pad (electrode) disposed at the central part thereof, and a second annular pad disposed so as to surround the first pad. Further, the connector of the extracorporeal device includes a third pad disposed at the central part thereof, and a fourth annular pad disposed so as to surround the third pad.

When the pair of connectors are coupled to each other, the first and third pads are opposed in a direction in which a universal cord extends, and approach each other. Further, when the connectors are coupled to each other, the second and fourth pads are opposed in a direction in which the universal cord extends, and approach each other.

Information about an image inside the living body is transferred from the intracorporeal device to the extracorporeal device by capacitive coupling between the first and third pads. A control signal is transferred from the extracorporeal device to the intracorporeal device by capacitive coupling between the second and fourth pads.

In the electronic endoscope system, the first and third pads are covered with an insulator. As such, even when the endoscope is cleaned using an antiseptic solution, these pads are prevented from being corroded. Accordingly, the endoscope is not only easily cleaned but is also prevented from being corroded.

SUMMARY OF THE INVENTION

According to a first aspect of the present invention, an endoscope system includes an endoscope having an insertion part capable of being inserted into the interior of a living body, an extracorporeal device configured to be installed outside the living body, a first extracorporeal signal connection part having a second electrode electrically connected to the extracorporeal device, and a first scope-side signal connection part that has a first electrode electrically connected to the endoscope, is engaged with the first extracorporeal signal connection part, and has a tubular shape. The insertion part includes an observation part allowed to observe a distal end side thereof. When engaged with the first scope-side signal connection part, the first extracorporeal signal connection part is wholly or partially disposed in an inner cylindrical space of the first scope-side signal connection part, and the second electrode and the first electrode are subjected to capacitive coupling.

Further, in the aspect of the present invention, the tubular shape includes not only a shape that is circular in a cross-sectional view of a parallel direction, long in an axial direction, and hollow, but also a shape in which a wall-shaped portion surrounding a hollow portion is partially cut out, i.e., a shape that is substantially C-shaped in a cross-sectional view of the parallel direction.

Further, the endoscope system may further include an extracorporeal power connection part having a second coil electrically connected with the extracorporeal device, and a scope-side power connection part that has a first coil electrically connected with the endoscope, is engaged with the extracorporeal power connection part, and has a tubular shape. When engaged with the scope-side power connection part, the extracorporeal power connection part may be wholly or partially disposed in an inner cylindrical space of the scope-side power connection part, and the second coil and the first coil may be subjected to electromagnetic coupling.

Further, the endoscope system may further include a second extracorporeal signal connection part that has a fourth electrode electrically connected with the extracorporeal device, and a second scope-side signal connection part that has a third electrode electrically connected with the endoscope, is engaged with the second extracorporeal signal connection part, and has a tubular shape. When engaged with the second scope-side signal connection part, the second extracorporeal signal connection part may be wholly or partially disposed in an inner cylindrical space of the second scope-side signal connection part, and the fourth electrode and the third electrode may be subjected to capacitive coupling. A signal based on the capacitive coupling between the fourth electrode and the third electrode may have a reverse phase with respect to a signal based on the capacitive coupling between the second electrode and the first electrode.

Also, in the endoscope system, the endoscope may be rotatable around a tubular axis of the first scope-side signal connection part with respect to the extracorporeal device.

Further, in the endoscope system, when the first extracorporeal signal connection part is engaged with the first scope-side signal connection part, a solid or liquid dielectric material having a relative permittivity of 1 or more may be disposed between the second electrode and the first electrode.

Further, in the endoscope system, the first extracorporeal signal connection part may be formed in a tubular shape and have an inner cylindrical space therein.

In addition, in the endoscope system, a light guide may be inserted into the inner cylindrical space.

DETAILED DESCRIPTION OF THE INVENTION

Figure 1:
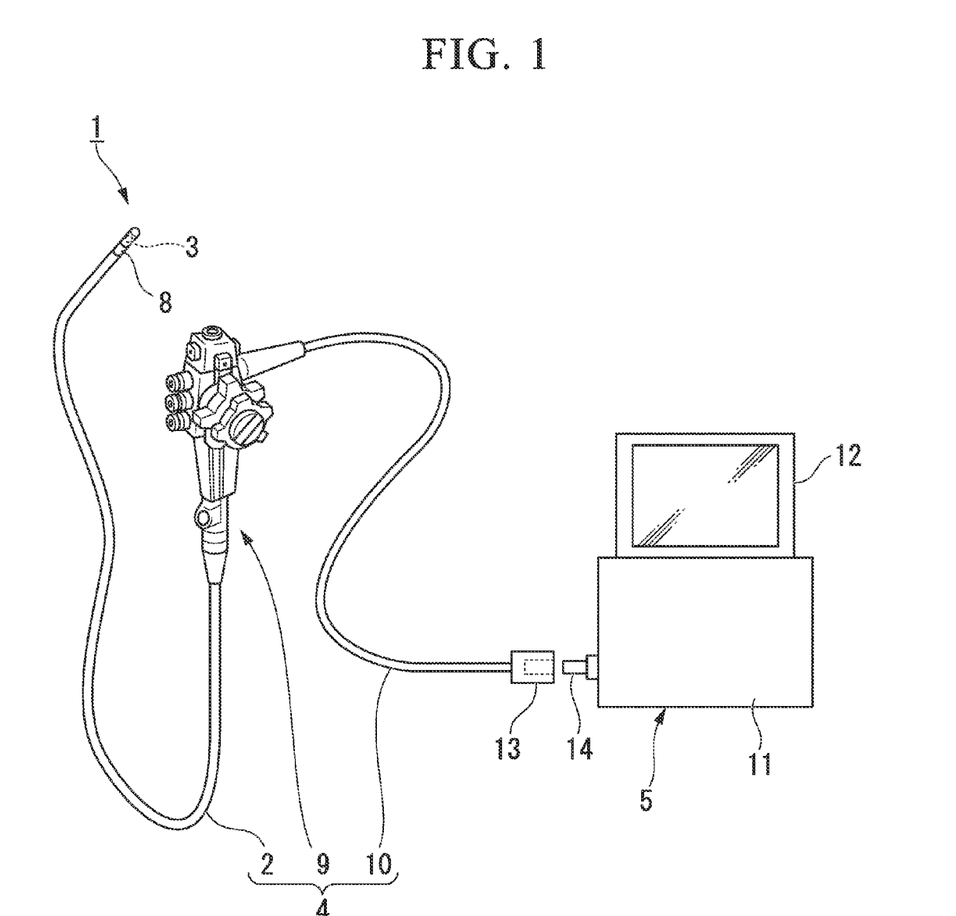
FIG. 1 is a diagram showing an entire configuration of an endoscope system according to an embodiment of the present invention.

Hereinafter, an endoscope system according to an embodiment of the present invention will be described with reference to FIGS. 1 to 7. As shown in FIG. 1 (the configuration diagram of an endoscope system), the endoscope system 1 is an instrument in which an insertion part 2 is inserted into a living body to observe the interior of the living body.

The endoscope system 1 of the present embodiment includes an endoscope 4 having the insertion part 2, and an extracorporeal device 5 installed outside the living body. The insertion part 2 is equipped with a charge-coupled device (CCD) (observation part) 3 that can observe a distal end side thereof.

The endoscope 4 is formed of a material having flexibility. The endoscope 4 includes the insertion part 2. The insertion part 2 is provided with a bending part 8 at a distal end thereof. The insertion part 2 is provided with a manipulation part 9 at a proximal end thereof. The manipulation part 9 is connected with an extracorporeal device 5 by a universal cord 10. The manipulation part 9 is equipped with an angle knob, and thus bends the bending part 8.

An illumination part (not shown) and the CCD 3 are installed on the distal end of the insertion part 2, i.e. a distal end side of the bending part 8. The illumination part used herein refers to a light collection optical system that illuminates the distal end side of the insertion part 2 with illumination light guided through, for example, a scope-side light guide 58 and an extracorporeal light guide 53 (to be described below).

The extracorporeal device 5 includes a main body part 11 acting as a base, and a display unit 12 displaying a video signal from the CCD 3. A scope-side connector 13 and an extracorporeal connector 14, which can be mutually connected or disconnected, are installed on a proximal end of the universal cord 10 and the main body part 11, respectively.

In the present embodiment, the connector part (the scope-side connector 13 and the extracorporeal connector 14) is installed between the proximal end of the universal cord 10 and the main body part 11, and the universal cord 10 is a part of the endoscope 4. However, if the connector part is installed between a distal end of the universal cord 10 (on the manipulation part 9 side) and the manipulation part 9, the universal cord 10 is included in the extracorporeal device 5, and thus is part of the extracorporeal device 5.

That is, on the observation part 3 side from a portion that is disconnected by the connector part becomes the endoscope, whereas on the main body part 11 side from the portion that is disconnected by the connector part becomes the extracorporeal device.

Further, the connector part may be installed on any portion between the universal cord 10 and the insertion part 2.

Figure 2:
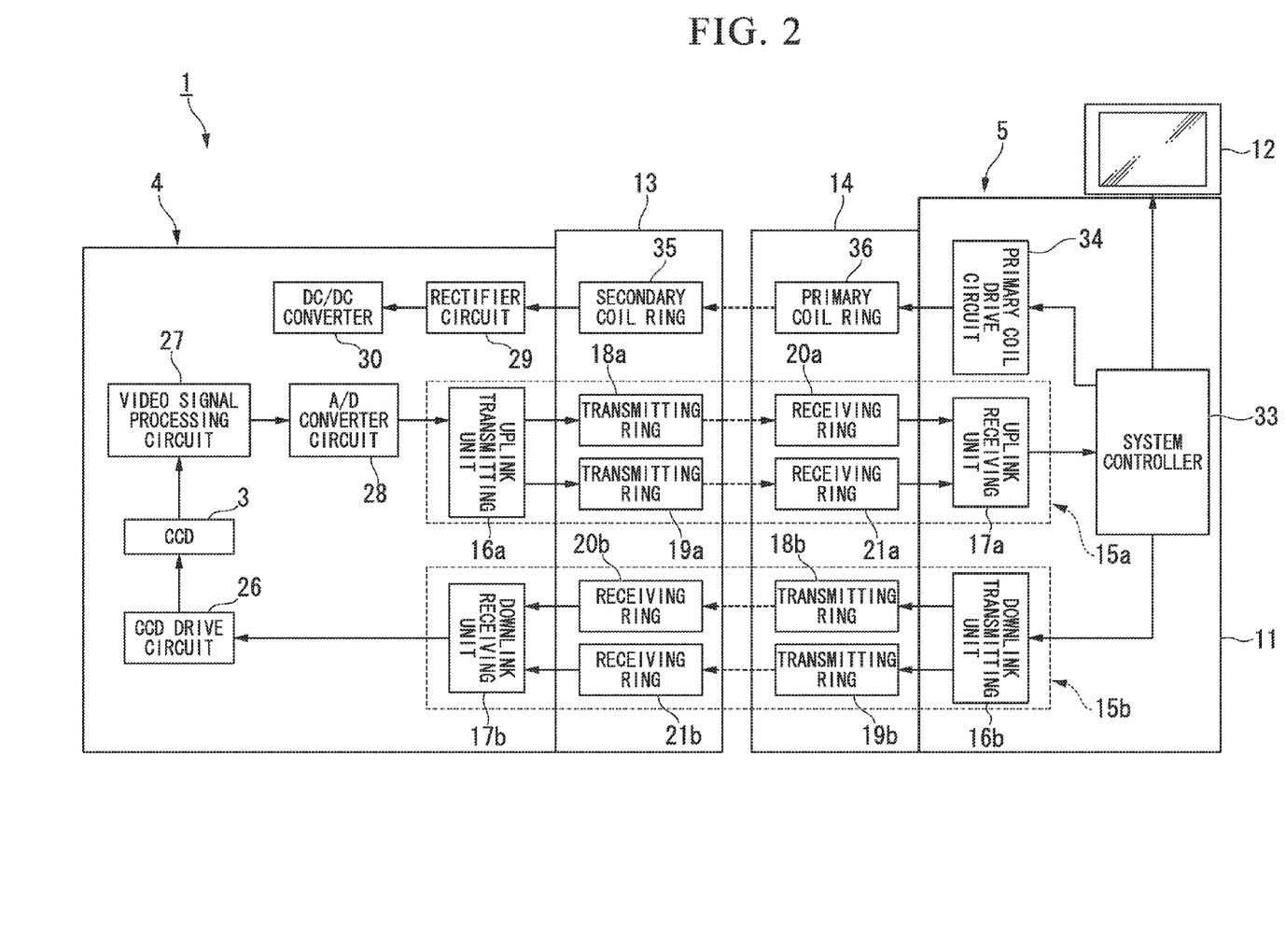
FIG. 2 is a block diagram showing the configuration of the endoscope system.

As shown in FIG. 2 (a block diagram of the endoscope system), the endoscope system 1 includes signal transmission parts 15a and 15b. The signal transmission parts 15a and 15b encode a signal, transfer the encoded signal by means of capacitive coupling, and decode the transferred signal. As will be described below, a signal is transferred from the endoscope 4 to the extracorporeal device 5 (uplink direction) by the signal transmission part 15a, while a signal is transferred from the extracorporeal device 5 to the endoscope 4 (downlink direction) by the signal transmission part 15b.

Since the signal transmission part 15a has the same configuration as the signal transmission part 15b, only the signal transmission part 15a will be described in detail. Further, the same numerals are assigned to the symbols of the corresponding components between the signal transmission part 15a and the signal transmission part 15b, and the elements of the signal transmission part 15a and the elements of the signal transmission part 15b are discriminated by assigning symbols "a" and "b" to respective numerals.

The endoscope 4 includes a CCD drive circuit 26 that controls driving of the CCD 3, a video signal processing circuit 27 that processes image data (video signal) captured by the CCD 3, an analog-to-digital (A/D) converter circuit 28 that converts an analog signal obtained by the video signal processing circuit 27 into a digital signal, a rectifier circuit 29 that converts alternating current into direct current, and a DC/DC converter 30 that adjusts a voltage of the direct current.

Further, the endoscope 4 further includes an uplink transmitting unit 16a that encodes and transmits a signal, and a downlink receiving unit 17b that decodes a received signal.

The main body part 11 includes a system controller 33 that controls the endoscope 4 and the extracorporeal device 5 to process the video signal, a primary coil drive circuit 34 that controls driving of a primary coil ring 36 (to be described below), an uplink receiving unit 17a that decodes a received signal, and a downlink transmitting unit 16b that encodes and transmits a signal.

The scope-side connector 13 includes a secondary coil ring (first coil) 35 that is supplied with power, a transmitting ring (first electrode) 18a and a transmitting ring (third electrode) 19a that transmit a signal by means of capacitive coupling, and a receiving ring (first electrode) 20b and a receiving ring (third electrode) 21b that receive a signal by means of capacitive coupling.

The extracorporeal connector 14 includes a primary coil ring (second coil) 36 that supplies power, a receiving ring (second electrode) 20a and a receiving ring (fourth electrode) 21a that receive a signal by means of capacitive coupling, and a transmitting ring (second electrode) 18b and a transmitting ring (fourth electrode) 19b that transmit a signal by means of capacitive coupling.

The signal transmission part 15a is constituted of the uplink transmitting unit 16a, the uplink receiving unit 17a, the transmitting ring 18a, the transmitting ring 19a, the receiving ring 20a, and the receiving ring 21a. The signal transmission part 15b is constituted of the downlink transmitting unit 16b, the downlink receiving unit 17b, the transmitting ring 18b, the transmitting ring 19b, the receiving ring 20b, and the receiving ring 21b.

Figure 3:
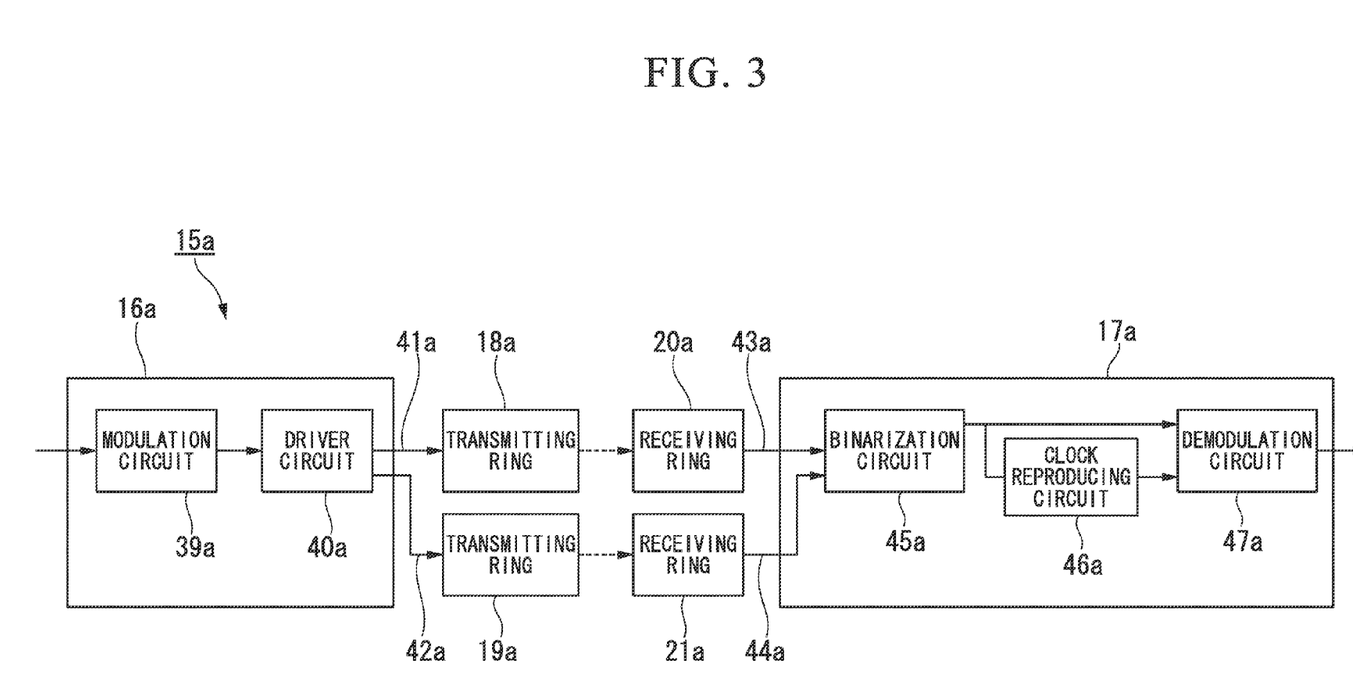
FIG. 3 is a block diagram showing a configuration of a signal transmitting part of the endoscope system.

Next, a detailed configuration of the signal transmission part 15a will be described.

As shown in FIG. 3 (block diagram of the signal transmission part 15a), the uplink transmitting unit 16a includes a modulation circuit 39a and a driver circuit 40a. The modulation circuit 39a modulates the digital signal (data) transmitted from the A/D converter circuit 28, and converts the modulated signal into a Manchester code. The driver circuit 40a is connected to the modulation circuit 39a, amplifies current of encoded data modulated by the modulation circuit 39a and current of reverse-phase data generated from the encoded data or performs impedance transformation, and outputs digital signals (data) to first ends of transmission lines 41a and 42a respectively.

The second ends of the transmission lines 41a and 42a are electrically connected to the transmitting rings 18a and 19a, respectively. The receiving rings 20a and 21a are electrically connected to first ends of transmission lines 43a and 44a.

The uplink receiving unit 17a includes a binarization circuit 45a that is connected to the second ends of the transmission lines 43a and 44a and detects levels of the data, a clock reproducing circuit 46a that is connected to the binarization circuit 45a and reproduces a clock from the encoded data, and a demodulation circuit 47a that is connected to the binarization circuit 45a and the clock reproducing circuit 46a and demodulates the encoded data. The video signal demodulated by the demodulation circuit 47a is transmitted to the system controller 33.

Figure 4:
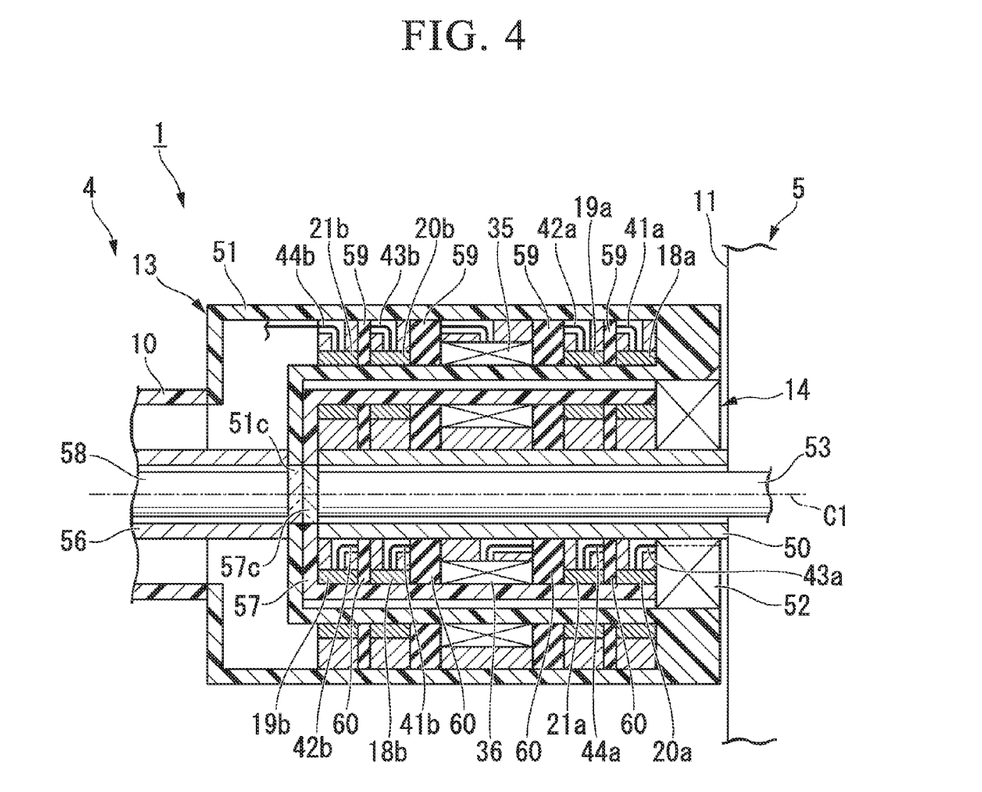
FIG. 4 is a cross-sectional diagram showing a connection of a scope-side connector and an extracorporeal connector of the endoscope system.

Next, configurations of the scope-side connector 13 and the extracorporeal connector 14 will be described.

As shown in FIG. 4 (cross-sectional diagram of the connector part), the extracorporeal connector 14 is formed in a columnar shape. The scope-side connector 13 is formed in a cylindrical shape so as to surround an outer circumferential surface of the extracorporeal connector 14. The scope-side connector 13 and the extracorporeal connector 14 can be connected by engaging the scope-side connector 13 to the extracorporeal connector 14. Further, the scope-side connector 13 and the extracorporeal connector 14 can be disconnected by releasing the engagement. When the scope-side connector 13 is connected to the extracorporeal connector 14, they are disposed on a common axis (axis of the cylinder) C1.

The extracorporeal connector 14 includes an extracorporeal shaft member 50 that is formed in a tubular shape and is disposed on the axis C1; receiving rings 20a and 21a, transmitting rings 18b and 19b, and a primary coil ring 36 that are formed in a cylindrical shape; a scope-side cladding member 57 that is installed so as to cover outer circumferential surfaces and ends of the receiving rings 20a and 21a, the transmitting rings 18b and 19b, and the primary coil ring 36 and is formed of a dielectric material; a bearing 52 that is formed in a ring shape, and an extracorporeal transparent glass 57c that guides light of an extracorporeal light guide 53 (to be described below) to a scope-side light guide 58 (to be described below).

The receiving rings 20a and 21a, the primary coil ring 36, and the transmitting rings 18b and 19b are disposed so as to extend along the axis C1, and are attached to support members formed of a material having an insulation property.

The receiving rings 20a and 21a, the primary coil ring 36, and the transmitting rings 18b and 19b are attached to a proximal end of the extracorporeal shaft member 50 via the support members so as to be arranged in that order from the side of the main body part 11 of the extracorporeal shaft member 50 to the side of the universal cord 10. Then, shield members 60 for interrupting an electromagnetic influence are installed between rings listed below.

a) Between the receiving ring 20a and the receiving ring 21a.

b) Between the receiving ring 21a and the primary coil ring 36.

c) Between the primary coil ring 36 and the transmitting ring 18b.

d) Between the transmitting ring 18b and the transmitting ring 19b.

The bearing 52 is installed so as to slightly protrude from the extracorporeal cladding member 57 in a radially outward direction, and is exposed from the extracorporeal cladding member 57. The bearing 52 is disposed so that outer and inner circumferential surfaces thereof run along the axis C1. Thus, the outer circumferential surface rotates around the axis C1 with a reduced frictional force with respect to the inner circumferential surface.

Further, the extracorporeal light guide 53, which guides illumination light generated from a light emitting device (not shown) installed inside the main body part 11, is inserted into the extracorporeal shaft member 50.

Figure 5:
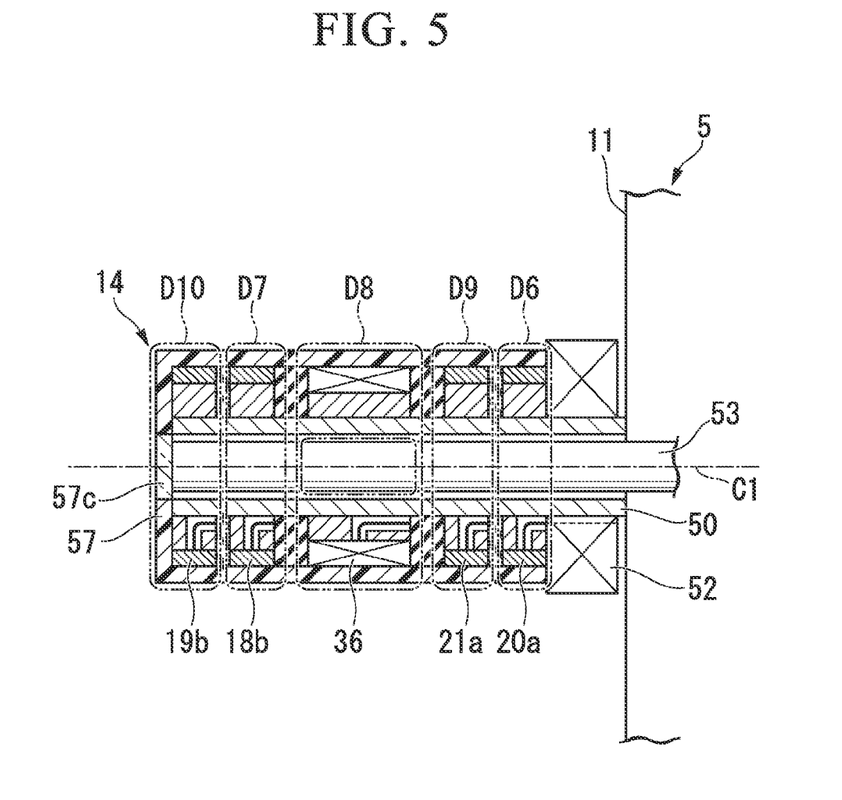
FIG. 5 is a cross-sectional diagram showing the extracorporeal connector of the endoscope system.

As shown in FIG. 5 (cross-sectional diagram of the extracorporeal connector), the extracorporeal connector 14 is integrally configured of first extracorporeal signal connection parts D6 and D7 having a receiving ring 20a as a second electrode and a transmitting ring 18b respectively, an extracorporeal power connection part D8 having a primary coil ring 36 as a second coil, and second extracorporeal signal connection parts D9 and D10 having a receiving ring 21a as a fourth electrode and a transmitting ring 19b.

The first extracorporeal signal connection parts D6 and D7, the extracorporeal power connection part D8, and the second extracorporeal signal connection parts D9 and D10 are each formed in a cylindrical shape, and have the same inner and outer diameters. The first extracorporeal signal connection parts D6 and D7, the extracorporeal power connection part D8, and the second extracorporeal signal connection parts D9 and D10 are disposed at relatively shifted positions in the direction of the axis C1 so that axes thereof match the axis C1.

The description will be made with reference to FIG. 4 again. The scope-side connector 13 includes a scope-side shaft member 56 that is formed in a tubular shape and is disposed on the axis C1, and transmitting rings 18a and 19a, receiving rings 20b and 21b, and a secondary coil ring 35 that are formed in a cylindrical shape, and is installed so as to cover inner and outer circumferential surfaces and ends of the transmitting rings 18a and 19a, the receiving rings 20b and 21b, and the secondary coil ring 35. Furthermore, the scope-side connector 13 includes a scope-side cladding member 51 formed of a dielectric material, and a scope-side transparent glass 51c that guides the light of the extracorporeal light guide 53 to the scope-side light guide 58 (to be described below).

The transmitting rings 18a and 19a, the secondary coil ring 35, and the receiving rings 20b and 21b are disposed so as to extend along the axis C1, and attached to respective support members formed of a material having an insulation property.

The transmitting rings 18a and 19a, the secondary coil ring 35, and the receiving rings 20b and 21b are installed in the scope-side cladding member 51 so as to be arranged in that order from the side of the main body part 11 to the side of the universal cord 10. Then, shield members 59 for interrupting an electromagnetic influence are installed between the transmitting ring 18a and the transmitting ring 19a, between the transmitting ring 19a and the secondary coil ring 35, between the secondary coil ring 35 and the receiving ring 20b, and between the receiving ring 20b and the receiving ring 21b.

Further, the scope-side light guide 58 is inserted in the scope-side shaft member 56 so as to guide the illumination light to the illumination part (not shown).

As the scope-side cladding member 57 and the extracorporeal cladding member 51, polycarbonate having a relative permittivity of 2.95 is used in the present embodiment.

Then, when the scope-side connector 13 and the extracorporeal connector 14 are connected, the receiving ring 20a and the transmitting ring 18a, the receiving ring 21a and the transmitting ring 19a, the primary coil ring 36 and the secondary coil ring 35, the transmitting ring 18b and the receiving ring 20b, and the transmitting ring 19b and the receiving ring 21b are disposed so as to face each other.

Figure 6:
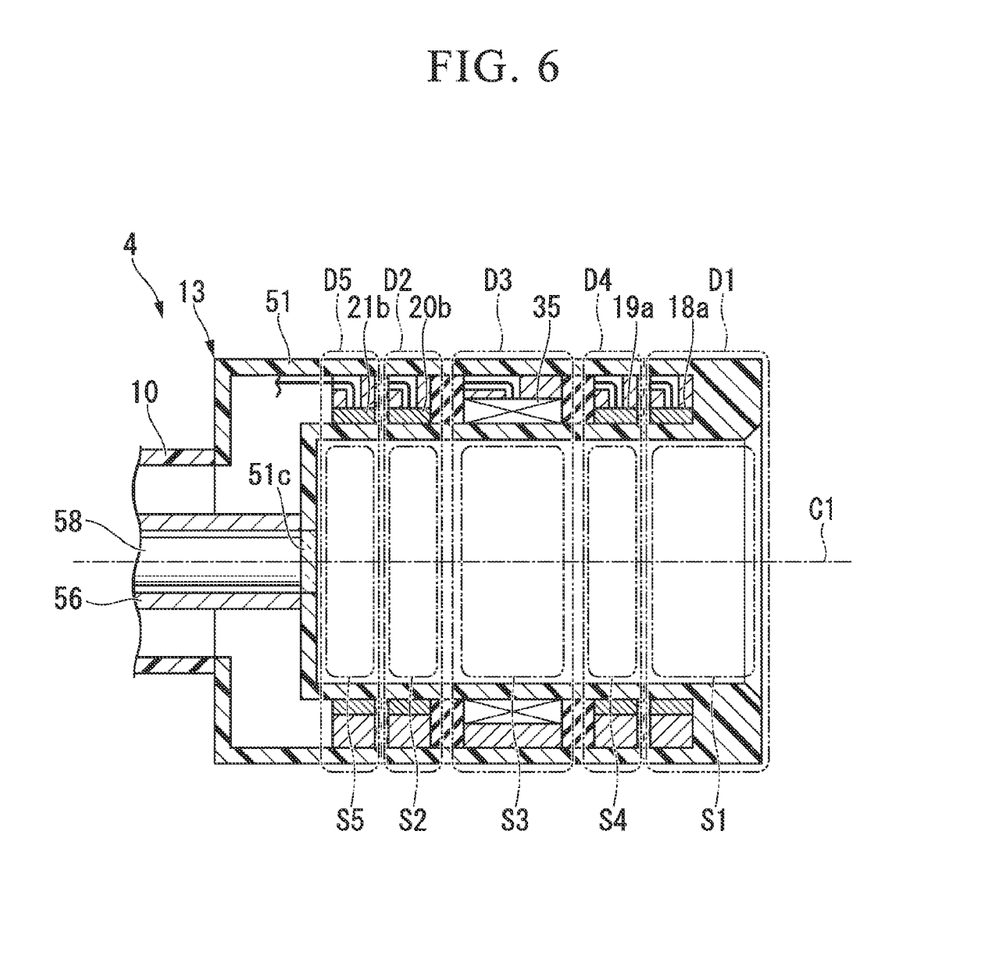
FIG. 6 is a cross-sectional diagram showing the scope-side connector of the endoscope system.

As shown in FIG. 6 (cross-sectional diagram of the scope-side connector), the scope-side connector 13 is integrally configured of first scope-side signal connection parts D1 and D2 having the transmitting ring 18a as a first electrode and the receiving ring 20b respectively, a scope-side power connection part D3 having the secondary coil ring 35 as a first coil, and second scope-side signal connection parts D4 and D5 having the transmitting ring 19a as a third electrode and the receiving ring 21b.

The first scope-side signal connection parts D1 and D2, the scope-side power connection part D3, and the second scope-side signal connection parts D4 and D5 are formed in a cylindrical shape, and thus have the same inner and outer diameters. The first scope-side signal connection parts D1 and D2, the scope-side power connection part D3, and the second scope-side signal connection parts D4 and D5 are disposed at relatively shifted positions in the direction of the axis C1 so that axes thereof match the axis C1.

That is, an inner cylindrical space S1 of the first scope-side signal connection part D1, an inner cylindrical space S2 of the first scope-side signal connection part D2, an inner cylindrical space S3 of the scope-side power connection part D3, an inner cylindrical space S4 of the second scope-side signal connection part D4, and an inner cylindrical space S5 of the second scope-side signal connection part D5 are disposed at relatively shifted positions in the direction of the axis C1 without overlapping.

Further, as shown in FIG. 4, when an inner circumferential surface of the scope-side cladding member 51 is installed on the outer circumferential surface of the bearing 52 with the axis of the scope-side connector 13 matched with the axis of the extracorporeal connector 14, the scope-side connector 13 is engaged and connected with the extracorporeal connector 14. In this case, the scope-side connector 13 is rotatable around the axis C1 with respect to the extracorporeal connector 14.

As shown in FIGS. 5 and 6, the scope-side connector 13 and the extracorporeal connector 14 are connected, thereby having the following configuration. The first extracorporeal signal connection part D6 is disposed in the inner cylindrical space 51 of the first scope-side signal connection part D1, and the receiving ring 20a and the transmitting ring 18a are subjected to capacitive coupling. The first extracorporeal signal connection part D7 is disposed in the inner cylindrical space S2 of the first scope-side signal connection part D2, and the transmitting ring 18b and the receiving ring 20b are subjected to capacitive coupling. The extracorporeal power connection part D8 is disposed in the inner cylindrical space S3 of the scope-side power connection part D3, and the primary coil ring 36 and the secondary coil ring 35 are subjected to electromagnetic coupling. The second extracorporeal signal connection part D9 is disposed in the inner cylindrical space S4 of the second scope-side signal connection part D4, and the receiving ring 21a and the transmitting ring 19a are subjected to capacitive coupling. The second extracorporeal signal connection part D10 is disposed in the inner cylindrical space S5 of the second scope-side signal connection part D5, and the transmitting ring 19b and the receiving ring 21b are subjected to capacitive coupling.

Further, as shown in FIG. 4, when the scope-side connector 13 and the extracorporeal connector 14 are connected, an end face of the scope-side light guide 58 is disposed so as to face an end face of the extracorporeal light guide 53. Thus, it is possible to transfer illumination light from the side of the extracorporeal light guide 53 to the scope-side light guide 58.

Next, an operation of each part of the signal transmission part 15a will be described.

Figure 7:
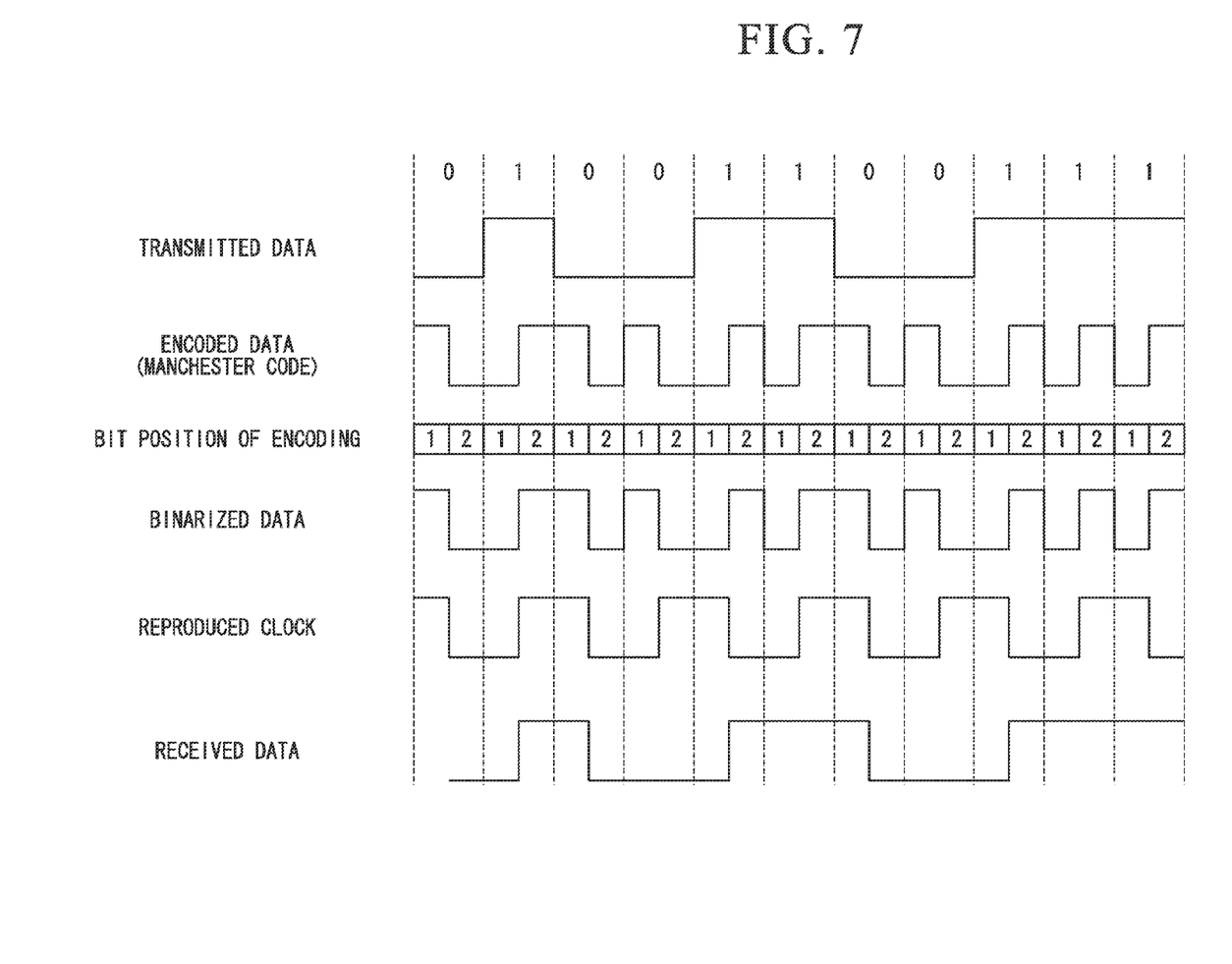
FIG. 7 is a timing diagram showing a signaling operation of the signal transmission part of the signal transmission device.

As shown in FIGS. 3 and 7 (time chart), the transmitted data that is the digital signal transferred from the A/D converter circuit 28 is converted into a Manchester code by the modulation circuit 39a. Thus, each transmitted data is modulated into two bits that are represented by a level of "1" or "0," so that encoded data is generated. The encoded data is transferred to the driver circuit 40a, and the driver circuit 40a generates reverse-phase data of the encoded data.

The encoded data is transferred to the receiving ring 20a by the capacitive coupling of the transmitting ring 18a and the receiving ring 20a. The reverse-phase data is transmitted to the receiving ring 21a by the capacitive coupling of the transmitting ring 19a and the receiving ring 21a. Then, the binarization circuit 45a detects a difference in level between the encoded data and the reverse-phase data, both of which are transferred, thereby removing noise included in both data. In addition, the binarization circuit 45a generates binarized data in which the level of each bit is represented by "1" or "0." The binarized data is transferred to the clock reproducing circuit 46a and the demodulation circuit 47a. In the clock reproducing circuit 46a, a reproduced clock is generated by timing of switching between a first bit and a second bit. The reproduced clock is transferred to the demodulation circuit 47a, and the demodulation circuit 47a demodulates the encoded data based on the reproduced clock, and generates received data.

Next, a process of transferring a signal, etc. between the endoscope 4 and the extracorporeal device 5 will be described. First, a process of transferring a signal and power from the extracorporeal device 5 to the endoscope 4 (downlink direction) will be described.

As shown in FIG. 2, the system controller 33 is connected to each of the downlink transmitting unit 16b, the uplink receiving unit 17a, the primary coil drive circuit 34, and the display unit 12.

When the system controller 33 sends a signal controlling the CCD 3 to the downlink transmitting unit 16b, the downlink transmitting unit 16b encodes the control signal to generate encoded data and reverse-phase data of the encoded data. The encoded data and the reverse-phase data are transferred by capacitive coupling of the transmitting ring 18b and the receiving ring 20b and capacitive coupling of the transmitting ring 19b and the receiving ring 21b, and are decoded by the downlink receiving unit 17b.

The decoded control signal is transferred to the CCD drive circuit 26 connected to the downlink receiving unit 17b. The CCD drive circuit 26 controls the CCD 3, which is connected therewith, based on the control signal.

On the other hand, when the system controller 33 sends the control signal to the primary coil drive circuit 34, the primary coil ring 36 electrically connected to the primary coil drive circuit 34 is supplied with a predetermined alternating current. Then, the alternating current flows to the secondary coil ring 35 by means of electromagnetic coupling of the primary coil ring 36 and the secondary coil ring 35. The alternating current is sent to the rectifier circuit 29 electrically connected to the secondary coil ring 35, and thus is converted to a direct current. The converted direct current is supplied to the CCD drive circuit 26, etc. by adjusting voltage through the DC/DC converter 30 connected to the rectifier circuit 29.

Next, a process of transferring a signal to the endoscope 4 or the extracorporeal device 5 (i.e. in an uplink direction) will be described.

A video signal captured by the CCD 3 is transferred to the video signal processing circuit 27 to which the CCD 3 is connected, and is processed into an analog signal. The analog signal is converted to a digital signal by the A/D converter circuit 28 connected to the video signal processing circuit 27. The converted digital signal is transferred to the uplink transmitting unit 16a connected to the A/D converter circuit 28.

The video signal transferred to the uplink transmitting unit 16a is encoded, so that encoded data and reverse-phase data of the encoded data are generated. The encoded data and the reverse-phase data are transferred by capacitive coupling of the transmitting ring 18a and the receiving ring 20a and capacitive coupling of the transmitting ring 19a and the receiving ring 21a, and are decoded by the uplink receiving unit 17a.

The decoded video signal is transferred from the uplink receiving unit 17a to the system controller 33, and is processed there. The processed video signal is sent to the display unit 12 and is displayed therein.

Thus, according to the endoscope system 1 of the embodiment of the present invention, the receiving ring 20a and the transmitting ring 18b, and the transmitting ring 18a and the receiving ring 20b disposed so as to face the receiving ring 20a and the transmitting ring 18b respectively are formed in a cylindrical shape and are disposed so as to extend along the axis C1.

Accordingly, even when the transmitting rings 18a and 18b and the receiving rings 20a and 20b are increased in area, an increase in outer diameters of the first scope-side signal connection parts D1 and D2 and the first extracorporeal signal connection parts D6 and D7 can be suppressed by disposing the rings 18a, 18b, 20a and 20b so as to further extend in the direction of the axis C1. Thus, it is possible to reliably transfer a signal between the transmitting ring 18a and the receiving ring 20a, and between the receiving ring 20b and transmitting ring 18b, both of which are capacitively coupled to each other.

Further, when the scope-side connector 13 and the extracorporeal connector 14 are connected, the secondary coil ring 35 installed on the scope-side power connection part D3 is subjected to electromagnetic coupling with the primary coil ring 36 installed on the extracorporeal power connection part D8 disposed in the inner cylindrical space S3 of the scope-side power connection part D3.

In this coupled state, the primary coil ring 36 is supplied with alternating current voltage. Thereby, an induced electromotive force occurs at the secondary coil ring 35 due to mutual induction. Accordingly, it is possible to supply power from the extracorporeal device 5 to the endoscope 4.

Further, the receiving ring 21a and the transmitting ring 19b, and the transmitting ring 19a and the receiving ring 21b disposed so as to face the receiving ring 21a and the transmitting ring 19b respectively are formed in cylindrical shapes, and are disposed so as to extend along the axis C1.

Accordingly, even when the transmitting rings 19a and 19b and the receiving rings 21a and 21b are increased in area, an increase in outer diameters of the second scope-side signal connection parts D4 and D5 and the second extracorporeal signal connection parts D9 and D10 can be suppressed by disposing the rings 19a, 19b, 21a and 21b so as to further extend in the direction of the axis C1.

Thus, the encoded data is transferred between the receiving ring 20a and the transmitting ring 18a that are capacitively coupled to each other. Further, the reverse-phase data of the encoded data is transferred between the receiving ring 21a and the transmitting ring 19a that are capacitively coupled to each other. A difference between the levels of both data is detected, and thereby it is possible to reduce the noise common to both signals, and thus to more reliably detect a signal.

Further, the scope-side connector 13 can rotate around the axis C1 with respect to the extracorporeal connector 14. For this reason, when the observation part 3 is rotated in the body of a patient while performing an operation, twisting of the endoscope 4 and the extracorporeal device 5 is prevented by the connector part, and thus it is possible to improve handling of the endoscope 4.

Further, the scope-side cladding member 51 and the extracorporeal cladding member 57 are installed on the surface of the scope-side connector 13 and the surface of the extracorporeal connector 14, respectively. For this reason, it is possible to reliably insulate the receiving ring 20a and the transmitting ring 18a, the transmitting ring 18b and the receiving ring 20b, the receiving ring 21a and the transmitting ring 19a, and the transmitting ring 19b and the receiving ring 21b, each of which are capacitively coupled to each other.

Further, the cladding members 51 and 57 are installed, thereby enabling stray capacitance between both electrodes to be increased compared to the case in which only air is filled between the electrodes. Accordingly, it is possible to enhance capacitive coupling between the electrodes and to more reliably transfer the signal.

In addition, the solid dielectric materials such as the cladding members 51 and 57 are used. Thereby, it is possible to stabilize the distances between the receiving ring 20a and the transmitting ring 18a, between the transmitting ring 18b and the receiving ring 20b, between the receiving ring 21a and the transmitting ring 19a, and between the transmitting ring 19b and the receiving ring 21b, and to further stabilize and transfer the signal.

Further, the scope-side light guide 58 and the extracorporeal light guide 53 can be disposed on the axes of the scope-side connector 13 and the extracorporeal connector 14. Thus, it is possible to guide the illumination light to the illumination part (not shown) by means of the light guides 53 and 58, and to illuminate the distal end of the insertion part.

Further, the extracorporeal signal connection parts D6, D7, D9 and D10 and the extracorporeal power connection part D8, and the scope-side signal connection parts D1, D2, D4 and D5 and the scope-side power connection part D3 are disposed at relatively shifted positions in the direction of the axis C1. Accordingly, it is possible to suppress an increase in the outer diameters of the scope-side connector 13 and the extracorporeal connector 14.

As described above, according to the endoscope system 1 of the present embodiment, the capacitive coupling is used to transmit the signal, and the electrodes are enclosed by the extracorporeal cladding member 57 and the scope-side cladding member 51. As such, even when the endoscope 4 is cleaned, the electrodes are not exposed to an antiseptic solution, and it is possible to prevent the electrodes from being corroded.

Further, since extracorporeal signal connection parts D6, D7, D9 and D10 and the extracorporeal power connection part D8 constituting the extracorporeal connector 14 are disposed in the inner cylindrical spaces S1 to S5 of the scope-side connector 13, the extracorporeal connector 14 can be formed in a columnar shape in which irregularity is small and can be easily wiped.

Further, in the present embodiment, the scope-side connector 13 is formed in a cylindrical shape, and the extracorporeal connector 14 is formed in a columnar shape. However, the scope-side connector 13 may be formed in a hollow elliptical shape or a hollow polygonal shape when viewed in its axial direction. Further, the scope-side connector 13 may be formed substantially in a C shape when viewed in its axial direction by removing part of a side of a cylinder in a lengthwise direction. Further, the extracorporeal connector 14 may be formed in an elliptical shape or a polygonal shape when viewed in its axial direction.

While the embodiment of the present invention has been described in detail with reference to the figures, specific configuration is not limited to this embodiment, and also includes a change in the configuration within a range without departing from the subject matter of the present invention.

For example, in the embodiment, the polycarbonate is used for the scope-side cladding member 51 and the extracorporeal cladding member 57. However, the scope-side cladding member 51 and the extracorporeal cladding member 57 may be formed of a solid or a liquid having a relative permittivity of 1 or more. Furthermore, all or only one of the scope-side cladding member 51 and the extracorporeal cladding member 57 may be provided.

Further, in the embodiment, the signal is modulated into the Manchester code. However, the method of modulating the signal is not limited to this, and thus another modulation method may be used.

Further, in the embodiment, when the endoscope 4 is equipped with a battery, and the battery supplies power to the CCD drive circuit 26, the scope-side power connection part D3 and the extracorporeal power connection part D8 may not be installed on the scope-side connector 13 and the extracorporeal connector 14.

In addition, in the embodiment, when the noise is small on transferring the signal, the receiving rings 21a and 21b and the transmitting rings 19a and 19b may not be provided.

While illustrative embodiments of the invention have been described, the invention is not limited to these embodiments. It will be understood by those skilled in the art that various additions, omissions, substitutions, and other modifications in configurations may be made therein without departing from the spirit and scope of the invention. Accordingly, the invention is not to be seen as limited by the foregoing description, but is only limited by the scope of the appended claims.

What is claimed is:

1. An endoscope system comprising:
   an endoscope capable of being inserted into an interior of a living body and having an insertion part;
   an extracorporeal device configured to be installed outside the living body;
   a first extracorporeal signal connection part having a second electrode electrically connected with the extracorporeal device; and
   a first scope-side signal connection part having a first electrode electrically connected with the endoscope, being engaged with the first extracorporeal signal connection part,
   wherein the insertion part includes an observation part capable of observing a distal end side thereof,
   wherein when engaged with the first scope-side signal connection part, the first extracorporeal signal connection part is at least partially disposed in an inner cylindrical space of the first scope-side signal connection part, and
   wherein the second electrode and the first electrode are coupled to each other via capacitive coupling.

2. The endoscope system according to claim 1, further comprising:
   an extracorporeal power connection part having a second coil electrically connected with the extracorporeal device; and
   a scope-side power connection part that has a first coil electrically connected with the endoscope, being engaged with the extracorporeal power connection part, and having a tubular shape,
   wherein, when engaged with the scope-side power connection part, the extracorporeal power connection part is at least partially disposed in an inner cylindrical space of the scope-side power connection part, and
   wherein the second coil and the first coil are coupled to each other via electromagnetic coupling.

3. The endoscope system according to claim 1, further comprising:
   a second extracorporeal signal connection part having a fourth electrode electrically connected with the extracorporeal device; and
   a second scope-side signal connection part having a third electrode electrically connected with the endoscope, being engaged with the second extracorporeal signal connection part, and having a tubular shape,
   wherein, when engaged with the second scope-side signal connection part, the second extracorporeal signal connection part is at least partially disposed in an inner cylindrical space of the second scope-side signal connection part,
   wherein the fourth electrode and the third electrode are coupled to each other via capacitive coupling, and
   wherein a signal based on the capacitive coupling between the fourth electrode and the third electrode has a reverse phase with respect to a signal based on the capacitive coupling between the second electrode and the first electrode.

4. The endoscope system according to claim 3,
   wherein a first shield member for interrupting electromagnetic influence is disposed between the second electrode and the fourth electrode, and a second shield member for interrupting electromagnetic influence is disposed between the first electrode and the third electrode.

5. The endoscope system according to claim 1, wherein the endoscope is rotatable around a tubular axis of the first scope-side signal connection part with respect to the extracorporeal device.

6. The endoscope system according to claim 1, wherein, when the first extracorporeal signal connection part is engaged with the first scope-side signal connection part, a solid or liquid dielectric material having a relative permittivity of 1 or more is disposed between the second electrode and the first electrode.

7. The endoscope system according to claim 1, wherein the first extracorporeal signal connection part is formed in a tubular shape and has an inner cylindrical space therein.

8. The endoscope system according to claim 7, wherein the inner cylindrical space has a light guide inserted thereinto.

9. The endoscope system according to claim 1,
   wherein the first scope-side signal connection part is a hollow cylinder, and wherein the first extracorporeal signal connection part is a cylinder which is concentrically disposed inside the inner cylindrical space of the first scope-side signal connection part.

10. The endoscope system according to claim 9, wherein the second electrode is provided on an outer cylindrical surface of the first extracorporeal signal connection part, and the first electrode is provided on an inner cylindrical surface of the first scope-side signal connection part.

* * * * *